US011312898B2

(12) United States Patent
Yang et al.

(10) Patent No.: US 11,312,898 B2
(45) Date of Patent: Apr. 26, 2022

(54) QUANTUM DOT AND PREPARATION METHOD THEREOF (71) Applicant: TCL TECHNOLOGY GROUP CORPORATION, Huizhou (CN)

(72) Inventors: Yixing Yang, Huizhou (CN); Zhiwen Nie, Huizhou (CN); Jielong Qiu, Huizhou (CN); Chengyu Yang, Huizhou (CN)

(73) Assignee: TCL TECHNOLOGY GROUP CORPORATION, Huizhou (CN)

( * ) Notice: Subject to any disclaimer, the term of this patent is extended or adjusted under 35 U.S.C. 154(b) by 263 days.

(21) Appl. No.: 16/325,045

(22) PCT Filed: Mar. 20, 2018

(86) PCT No.: PCT/CN2018/079626
§ 371 (c)(1),
(2) Date: Feb. 12, 2019

(87) PCT Pub. No.: WO2019/010999
PCT Pub. Date: Jan. 17, 2019

(65) Prior Publication Data
US 2020/0308478 A1 Oct. 1, 2020

(30) Foreign Application Priority Data

Jul. 11, 2017 (CN) .......................... 201710560387.X
Jul. 11, 2017 (CN) .......................... 201710560424.7

(51) Int. Cl.
C09K 11/02 (2006.01)
C09K 11/70 (2006.01)
C09K 11/88 (2006.01)
H01L 51/50 (2006.01)
B82Y 20/00 (2011.01)
B82Y 30/00 (2011.01)
B82Y 40/00 (2011.01)

(52) U.S. Cl.
CPC ............ C09K 11/02 (2013.01); C09K 11/025 (2013.01); C09K 11/70 (2013.01); C09K 11/883 (2013.01); H01L 51/502 (2013.01); B82Y 20/00 (2013.01); B82Y 30/00 (2013.01); B82Y 40/00 (2013.01)

(58) Field of Classification Search
CPC ....... C09K 11/02; C09K 11/70; C09K 11/883; C09K 11/025; B82Y 20/00; B82Y 30/00; B82Y 40/00
See application file for complete search history.

(56) References Cited

U.S. PATENT DOCUMENTS

| 3,803,188 A * | 4/1974 | Scott et al. ........... C07C 51/412 554/75 |
| 7,387,833 B2 | 6/2008 | Reiss et al. |
| 8,153,022 B2 * | 4/2012 | Ryowa ................... C09K 11/62 252/301.33 |
| 8,323,595 B1 * | 12/2012 | Smith .................... H01M 10/54 423/89 |
| 9,666,768 B2 * | 5/2017 | Daniels ................. H01L 33/502 |
| 2007/0042576 A1 * | 2/2007 | Chan ...................... C09K 11/02 438/497 |
| 2011/0017951 A1 | 1/2011 | Ryowa |
| 2014/0001405 A1 * | 1/2014 | Guo ...................... C09K 11/025 252/301.33 |
| 2016/0308261 A1 * | 10/2016 | Tyagi ........................ C22B 3/02 |
| 2017/0362255 A1 * | 12/2017 | Beard .................. C09K 11/025 |
| 2020/0343489 A1 * | 10/2020 | Park ........................ H01L 33/06 |

FOREIGN PATENT DOCUMENTS

| CN | 101130693 A | 2/2008 |
| CN | 100529013 C | 8/2009 |
| CN | 101906298 A | 12/2010 |
| CN | 106367060 * | 1/2017 |
| CN | 106479503 A | 3/2017 |
| CN | 106544018 A | 3/2017 |
| CN | 106566318 * | 4/2017 |
| CN | 106601886 A | 4/2017 |
| JP | 2015511167 A | 4/2015 |
| WO | 2014181245 A1 | 11/2014 |
| WO | WO 2014/181245 * | 11/2014 |
| WO | 2017082116 A1 | 5/2017 |
| WO | WO 2018/101536 * | 6/2018 |

OTHER PUBLICATIONS

Translation for CN 106367060, Jan. 2, 2017.*
Translation for CN 106566318, Apr. 19, 2017.*
Zachary Lingley el al "A High Quantum Efficiency Preserving Approach To Ligand Exchange On Lead Sulfide Quantum Dots and Interdot Resonant Energy Transfer." Nano Letters 11.7 (Jun. 27, 2011): pp. 2887-2891.*
The World Intellectual Property Organization (WIPO) International Search Report for PCT/CN2018/079626 dated Jun. 1, 2018 7 Pages.
Francesca Pietra et al. "Ga for Zn Cation Exchange Allows for Highly Luminescent and Photostable InZnP-Based Quantum Dots." Chemistry of Materials 29.12 (2017): 5192-5199.
Yanpei Li et al. "ZnCdS/CdxZn1-xSeyS1-y Quantum Dot Quantum Well and Organic-Inorganic LEDs." Micronanoelectronic Technology, vol. 52, No. 6, Jun. 2015, pp. 348-354.

(Continued)

Primary Examiner — C Melissa Koslow
(74) Attorney, Agent, or Firm — Anova Law Group, PLLC (57) ABSTRACT The present disclosure discloses a quantum dot and a preparation method thereof, the method comprises a plurality of following steps: preparing a quantum dot solution; preparing an ion-containing organic ligand precursor; adding the ion-containing organic ligand precursor into the quantum dot solution, and making a surface-modification to the quantum dots, before obtaining the quantum dots having the surfaces modified; or providing a quantum dot solution; providing an ion-containing organic ligand precursor; mixing the ion-containing organic ligand precursor and the quantum dot solution, to make a ligand exchanging, before centrifuging and obtaining the quantum dots having the ligand exchanged.

11 Claims, 2 Drawing Sheets (56) References Cited

OTHER PUBLICATIONS

Zachary Lingley et al. "A High Quantum Efficiency Preserving Approach To Ligand Exchange On Lead Sulfide Quantum Dots and Interdot Resonant Energy Transfer." Nano Letters 11.7 (2011): 2887-2891.

* cited by examiner

QUANTUM DOT AND PREPARATION METHOD THEREOF

CROSS-REFERENCES TO RELATED APPLICATIONS

This application is a national stage application of PCT Patent Application No. PCT/CN2018/079626, filed on Mar. 20, 2018, which claims priority to Chinese Patent Application No. 201710560387.X, filed on 11 Jul. 2017, the content of all of which is incorporated herein by reference.

TECHNICAL FIELD

The present invention generally relates to the field of quantum dot technology and, more particularly, relates to a quantum dot and a preparation method thereof.

BACKGROUND

A remarkable quantum confinement effect of a quantum dot (QD) leads to a plurality of unique nano-properties thereof, such as continuously-adjustable emission wavelength, narrow emission wavelength, wide absorption spectrum, high emission intensity and long fluorescence lifetime, etc. These unique properties make the QDs have a wide application prospect in a plurality of optoelectronic fields including flat panel display, solid state lighting, photovoltaic solar energy, etc.

A size of a QD is generally less than 20 nm, thus a QD material owns a very large specific surface area, a surface character and a property of a QD has a significant effect on a performance of the QD. There are a plurality of dangling bonds on a surface of the QD, wherein some of the dangling bonds are connecting to an organic ligand added to a reaction process (such as an organic amine, an organic carboxylic acid, an organic phosphine, a mercaptan, etc.), other dangling bonds are exposing to an outer environment, and are easy to react with an external environment, while an exposed dangling bond may form a defect state and a defect energy level in an energy band gap, which is also an important reason causing a non-radiative transition loss and a luminous efficiency decrease of a QD. Therefore, a plurality of exposed dangling bonds on the surface of the QDs shall be eliminated as much as possible.

Generally, there are two methods to eliminate the exposed dangling bonds on the surface of the QDs and passivate the QDs effectively: one is achieved by connecting an organic ligand to the exposed dangling bond; another is achieved by continuously growing an inorganic outer shell layer out of the exposed dangling bonds. However, either method has a certain limitation: in the first method, since the organic ligand is easy to get desorption, and it is hard to quantitatively control a binding degree and a binding amount of the organic ligands on the surfaces of the QDs, thus it is hard to effectively passivate the surfaces of the QDs; while in the second method, continuously growing the inorganic outer shell layer can effectively eliminate the exposed dangling bonds near the QD core, and the method is reproducible and easy to control, however a plurality of surfaces of the outer shell layer grown still has inevitably the exposed dangling bonds, thus the luminous efficiency of the QD is still getting effected. Generally, a preparation of a high-quality QD may combine both methods to eliminate the exposed dangling bonds on surfaces as much as possible, that is, after a certain thickness of the inorganic outer shell layer has grown on the surfaces of the QDs, the organic ligands are added for bonding, so as to eliminate the exposed dangling keys on the surfaces of the inorganic outer shell layer.

However, in such a combination scheme, the effective binding of the organic ligands to the exposed dangling bonds on the surfaces of the QD shell layer still has a plurality of problems: a main reason is that there is a certain selectivity in the binding of the organic ligands to the surface atoms of the QDs, thus a specific organic ligand may tend to bind to a specific atom of the surfaces. Therefore, on one hand, it is necessary to finely control a plurality of reaction conditions, before being able to achieve an effective binding of a free organic ligand in the system to the a desired surface atom of the QDs, thereby eliminating the exposed dangling bonds; on an other hand, a plurality of exposed dangling bonds of the atoms of the surfaces that the organic ligands are not inclined to bond may be impossible to get eliminated.

Thus, it is necessary to develop a more efficient QD preparation method, so as to eliminate the surface defect state generated by the exposed dangling bonds on the surfaces of the QDs, so as to improve a luminescent property of a QD material.

BRIEF SUMMARY OF THE INVENTION

In view of the above problems in the existing technology, the objective of the present invention is to provide a QD and a preparation method thereof, so as to solve the problem that the exposed dangling bonds on the surfaces of the QDs are impossible to be eliminated effectively, causing a plurality of surface defect states are generated, thus effecting the property of the QDs.

The technical solution of the present invention is as follows:

A preparation method of a QD, wherein comprising:
preparing a QD solution;
preparing an ion-containing organic ligand precursor;
adding the ion-containing organic ligand precursor into the QD solution, and making a surface-modification to the QDs, before obtaining the QDs having the surfaces modified.

The preparation method of the QD, wherein the QDs in the QD solution are at least one QD in groups of II-VI, groups of III-V, and groups of IV-VI.

The preparation method of the QD, wherein a structure of the QDs in the QD solution is at least one of a homogenous multi-alloy component mononuclear structure, a multi-alloy component gradient mononuclear structure, a multi-alloy component discrete core-shell structure, a multi-alloy component gradient core-shell structure.

The preparation method of the QD, wherein the ion-containing organic ligand precursor is at least one cation-containing organic ligand precursor, a cation in the cation-containing organic ligand precursor is at least a cation in a group of IIB, a group of IIIA, a group of IVA, a group of IB, a group of IIIA, a transition metal cation, a rare-earth metal cation.

The preparation method of the QD, wherein the ion-containing organic ligand precursor is at least one anion-containing organic ligand precursor, an anion in the anion-containing organic ligand precursor is at least an anion in a group of VIA, a group of VA, a group of VIIA.

The preparation method of the QD, wherein an organic ligand in the ion-containing organic ligand precursor is at least one of an organic phosphine, an organic acid, an organic amine, and an alkyl mercaptan.

The preparation method of the QD, wherein mixing anionic precursor and the organic ligand for a reaction, and the ions in the ionic precursor are combined with the organic ligand to prepare the ion-containing organic ligand precursor.

The preparation method of the QD, wherein mixing the ionic precursor and the organic ligand at a molar ratio of an ionic element to the organic ligand of 1:0.1 to 1:10 for a reaction; a temperature of the reaction is 20-400° C., and a time is 5 minutes to 10 hours, and/or an atmosphere of the reaction is one of an inert atmosphere, an air atmosphere, and a vacuum.

The preparation method of the QD, wherein mixing the ion-containing organic ligand precursor and the QD at a mass ratio of (0.01-100):1 to make the surface-modification; a temperature of a reaction of the surface-modification is 10-400° C., a time is 5 minutes to 10 hours, an atmosphere is one of an inert atmosphere, an air atmosphere, and a vacuum.

A preparation method of a QD, wherein comprising:
providing a QD solution;
providing an ion-containing organic ligand precursor;
mixing the ion-containing organic ligand precursor and the QD solution, to make a ligand exchanging, before centrifuging and obtaining the QDs having the ligand exchanged.

The preparation method of the QD, wherein the QDs in the QD solution are at least one QD in groups of II-VI, groups of III-V, and groups of IV-VI.

The preparation method of the QD, wherein a structure of the QDs in the QD solution is at least one of a homogenous multi-alloy component mononuclear structure, a multi-alloy component gradient mononuclear structure, a multi-alloy component discrete core-shell structure, a multi-alloy component gradient core-shell structure.

The preparation method of the QD, wherein the ion-containing organic ligand precursor is at least one cation-containing organic ligand precursor, a cation in the cation-containing organic ligand precursor is at least a cation in a group of IIB, a group of IIIA, a group of IVA, a group of IB, a group of IIIA, a transition metal cation, a rare-earth metal cation.

The preparation method of the QD, wherein the ion-containing organic ligand precursor is at least one anion-containing organic ligand precursor, an anion in the anion-containing organic ligand precursor is at least an anion in a group of VIA, a group of VA, a group of VIIA.

The preparation method of the QD, wherein an organic ligand in the ion-containing organic ligand precursor is at least one of an organic phosphine, an organic acid, an organic amine, and an alkyl mercaptan.

The preparation method of the QD, wherein mixing the ion-containing organic ligand precursor and the QD at a mass ratio of (0.01-100):1 to make the ligand exchanging, and/or a reaction temperature of the ligand exchanging is 10-400° C., and a time is 5 minutes to 10 hours, an atmosphere of the ligand exchanging is one of an inert atmosphere, an air atmosphere, and a vacuum.

A QD, wherein the QD comprises a QD core and an ion-containing organic ligand, and an exposed dangling bond on the surface of the QD core is combined with an ion in the ion-containing organic ligand.

The QD, wherein the QD comprises a QD core and a cation-containing organic ligand, and an exposed dangling bond on the surface of the QD core is combined with a cation in the cation-containing organic ligand.

The QD, wherein the QD comprises a QD core and an anion-containing organic ligand, and an exposed dangling bond on the surface of the QD core is combined with an anion in the anion-containing organic ligand.

Benefits: The present invention makes the surface-modification to the QDs newly prepared by the ion-containing organic ligand precursor, or by adding a previously prepared ion-containing organic ligand precursor to an existing QD solution, and making an effective ligand exchange on the surfaces of the QD through the ion-containing organic ligand precursor, on one hand, it is possible to effectively reduce a number of the dangling bonds existing on the surfaces of the QDs, and on other hand, since the ion combined with the exposed dangling bond has already connected itself to an organic ligand molecule, thus no new exposed dangling bonds will be introduced at a same time of binding, being able to effectively suppressing a defect state and a defect level, reducing a non-radiative transition loss, thereby improving a luminous efficiency of the QDs.

DETAILED DESCRIPTION

The present invention provides a QD and a preparation method thereof. To make the objectives, technical schemes and results more explicit, further description will be made in detail to illustrate the present invention. It should be understood that the specific embodiments described herein are only used to explain the present invention, and are not intended to limit the scope of the present invention.

A dangling bond is formed by a crystal lattice in a crystal (such as a QD) suddenly terminates at a surface, and each atom in an outermost layer of the surface will have an unpaired electron, that is, an unsaturated bond. In some embodiments, a QD having a ZnS outer shell layer forms an S atom dangling bond with an unsaturated bond on the surface; since the QD has a pretty large specific surface area, thus a large number of surface atoms and a plurality of dangling bonds correspondingly are existing on the surfaces of the QDs. After completing a conventional QD preparation reaction, there are a large number of dangling bonds on the surfaces of the QD, wherein some of the dangling bonds are connecting to a plurality of organic molecules added during the reaction process (such as organic amine, organic carboxylic acid, organic phosphinea mercaptan, etc.), while other dangling bond is exposed to an external environment and formed an exposed dangling bond. The exposed dangling bond is easy to react with an external environment, while forming a defect state and a defect energy level in a bond gap, and this is also an important reason causing a non-radiative transition loss. Thus the surfaces of the QDs need an effective modification, to add a number of the ligands on the surface of the QD, and to enhance a degree of binding of the QDs to the surface ligands, so as to eliminating the exposed dangling bonds on the surfaces of the QDs as much as possible. A plurality of embodiments achieve a purpose of eliminating the exposed dangling ponds on the surfaces of the QDs, by adding the ion-containing organic ligand precursor to a newly prepared QD solution, and using the ion-containing organic ligand precursor to react with the QDs.

Specifically, a preparation method of the QDs, wherein comprising:

preparing a QD solution;

preparing an ion-containing organic ligand precursor;

adding the ion-containing organic ligand precursor into the QD solution, and making a surface-modification to the QDs, before obtaining the QDs having the surfaces modified.

A surface-modification method disclosed in some embodiments makes the surface-modification to the QDs newly prepared by the ion-containing organic ligand precursor, on one hand, it is possible to effectively reduce a number of the dangling bonds existing on the surfaces of the QDs, and on other hand, since the ion combined with the exposed dangling bond has already connected itself to an organic ligand molecule, thus no new exposed dangling bonds will be introduced at a same time of binding, being able to effectively suppressing a defect state and a defect level, reducing a non-radiative transition loss, thereby improving a luminous efficiency of the QDs.

The QD solution may be a reaction system untreated after completing a conventional QD preparation reaction; or a solution system in which the QD conventionally prepared is redispersed in an organic solvent. The organic solvent includes at least one of chloroform, toluene, chlorobenzene, n-hexane, n-octane, decalin, tridecane, TOP, TBP, ODE, OA, ODA, TOA, OAm and more.

The QD in the QD solution may beat least one QD in groups of II-VI, groups of III-V, and groups of IV-VI.

A structure of the QDs in the QD solution may be at least one of a homogenous multi-alloy component mononuclear structure, a multi-alloy component gradient mononuclear structure, a binary component discrete core-shell structure, a multi-alloy component discrete core-shell structure, a multi-alloy component gradient core-shell structure.

A core or shell compound in the structure of the QDs described above includes at least one of CdSe, CdS, ZnSe, ZnS, CdTe, ZnTe, CdZnS, CdZnSe, CdZnTe, ZnSeS, ZnSeTe, ZnTeS, CdSeS, CdSeTe, CdTeS, CdZnSeS, CdZnSeTe, CdZnSTe, CdSeSTe, ZnSeSTe, CdZnSeSTe in groups of II-VI; at least one of InP, GaP, GaAs, InAs, InAsP, GaAsP, InGaP, InGaAs, InGaAsP in groups of III-V; at least one of PbS, PbSe, PbTe, PbSeS, PbSeTe, PbSTe in groups of IV-VI.

The ion-containing organic ligand precursor in some embodiments is prepared by a method described below: mixing an ionic precursor with an organic ligand before reacting, an ion in the ionic precursor combines with an organic ligand to prepare the ion-containing organic ligand precursor.

Wherein, mixing the ionic precursor with the organic ligand at a molar ratio of 1:0.1 to 1:10 respectively, and a preferred ratio range is from 1:0.5 to 1:5. A reaction temperature is 20-400° C., a preferred temperature range is a room temperature of 25° C. to 300° C.; a reaction time is 5 minutes to 10 hours, a preferred time range is 5 minutes to 60 minutes; a reaction atmosphere is one of an inert atmosphere, an air atmosphere and a vacuum (a pressure <100 Pa), a preferred atmosphere is an inert atmosphere, such as an inert atmosphere of a nitrogen or an argon.

In one specific embodiment, the ion-containing organic ligand precursor is at least one cation-containing organic ligand precursor. Wherein the cation may be a cation in a group of IIB, such as Cd, Zn, an Hg and more; may also be a cation in a group of IIIA, such as In, Ga, Al, and more; may also be a cation in a group of IVA, such as Pb, Sn and more; may be a cation in a group of IB, such as Cu, Ag, Au and more. The cation may be a transition metal cation, such as Mn, Fe, Co, Ni, Pd, Pt, Y, Mo, Cr, V and more. The cation may be at least one of a rare-earth metal cation. Preferably, the cation is one of the group of IIB, the group of IIIA, the group of IVA.

In a specific embodiment, at least one cationic precursor with the organic ligand is mixed and reacted, before the cation-containing organic ligand precursor is prepared. A selection of the cationic precursor in the embodiments has no limitation, for example, the cationic precursor may be an oxide of the cation, including but not limited to, CdO, ZnO, or an organic acid of the cation, including but not limited to, $Zn(OA)_2$, $Cd(OA)_2$, $Pb(OA)_2$, $In(OA)_3$, zinc diethyldithiocarbamate.

The cation in the cationic precursor reacts and combines with an organic ligand molecule before forming the cation-containing organic ligand precursor (for example, in some specific embodiments, a structure of the cation-containing organic ligand precursor is A1-B1, wherein the A1 is an ion, and the B1 is an organic precursor.).

An action mechanism of adopting the cation-containing organic ligand precursor to make a surface-modification to the QDs is: when adding the cation-containing organic ligand precursor to the QD solution system, the cation will combine with the exposed dangling bonds existing on the surfaces of the QDs, while an organic ligand molecule having combined with the cation will also combine to the surfaces of the QDs, meanwhile, thus a combination of the organic ligand and the dangling bond is realized, before obtaining a QD having the surfaces modified and the exposed dangling bond eliminated. In a specific embodiment, the ion-containing organic ligand precursor is at least one anion-containing organic ligand precursor. Wherein the anion may be an anion in a group of VIA, such as an S, an Se, a Te and more; may also be an element of a group of VA, such as a P, an As and more. The anion may be an anion in a group of VIIA, such as a Cl, a Br, an I and more.

In some specific embodiments, mixing at least one anionic precursor with an organic ligand before reacting, and the anion-containing organic ligand precursor is prepared. A selection range of the anionic precursors is pretty wide, including but not limited to, an elementary substance of the above elements in various groups.

The anion in the anionic precursor reacts and combines with an organic ligand molecule before forming the anion-containing organic ligand precursor (for example, in some specific embodiments, a structure of the anion-containing organic ligand precursor is A2-B2, wherein the A2 is an anion, and the B2 is an organic precursor.).

An action mechanism of adopting the anion-containing organic ligand precursor to make a surface-modification to the QDs is: when adding the anion-containing organic ligand precursor to the QD solution system, the anion will combine with the exposed dangling bonds existing on the surfaces of the QDs, while an organic ligand molecule having combined with the anion will also combine to the surfaces of the QDs at a same time, thus a combination of the organic ligand and the dangling bond is realized, before obtaining a QD having the surfaces modified and the exposed dangling bond eliminated.

Wherein the organic ligand may be an organic phosphine, such as trioctylphosphine (TOP), tributylphosphine (TBP), trioctylphosphine oxide (TOPO), octadecylphosphonic acid (ODPA). The organic ligand may be an organic acid, such as oleic acid (OA), stearic acid, palmitic acid, myristic acid. The organic ligand may be an organic amine, such as octadecylamine (ODA), Trioctylamine (TOA), oleylamine (OAm). The organic ligand may be an alkyl mercaptan, such as an octadecylmercaptan, an octathiol. The organic ligand maybe a 1-Octadecene (ODE).

The method of surface-modification, wherein a mass ratio of the ion-containing organic ligand precursor to the QD is (0.01-100):1, a preferred ratio range is (0.05-10):1. A temperature of the surface-modification is 10-400° C., a preferred range of the temperature is the room temperature of 25° C. to 380° C.; a time of the surface-modification is 5 minutes to 10 hours, a preferred range of the time is 5 minutes to 60 minutes; an atmosphere of the surface-modification is an inert atmosphere, such as a nitrogen or an argon.

By adding an ion-containing organic ligand precursor to the QD solution, the ion-containing organic ligand precursor may combine with the exposed dangling bonds on the surfaces of the QDs, thereby achieving a purpose of eliminating the exposed dangling bond on the surfaces of the QD as much as possible. A reduction of the exposed dangling bonds on the surfaces of the QDs in the embodiments, may improve a luminous efficiency of the QDs themselves, additionally, introducing more organic ligands and bound more closely on the surfaces of the QDs, may effectively enhance a colloidal stability and a dissolution dispersibility of the QDs in the solvent, especially in an ink solvent system.

Comparing to a traditional method, the preparation method described above is: an organic ligand molecule to be used for a reaction with the QDs is first reacted and combined with an ion in the ionic precursor alone (for example, a cation or an anion in some embodiments), before mixing the organic ligand precursor having the ions bound with the QD solution, followed by reacting the above reagent, that is, introducing the organic ligand molecule is actually achieved by combining the ions (such as the cations or the anions) and the dangling bonds; Thus, on one hand, an extremely strict and fine reaction condition control of the organic ligands molecule reacting and combining directly with the QD material may be avoided, and on other hand, a problem that the organic ligand molecules are selective when combining to a plurality of surface atoms of the QDs is solved. Meanwhile, the method described above may effectively reduce a number of the dangling bonds existing on the surfaces of the QDs on one hand, and on other hand, since the ions combining with the exposed dangling bonds themselves have already connected to the organic ligand molecules (since they are added to the system in a form of the organic ligand precursor combined with ions), thus no new exposed dangling bonds will be introduced at a same time of the combination, thus it is able to effectively suppressing a defect state and a defect level, reducing a non-radiative transition loss, thereby improving a luminous efficiency of the QDs. Also, the newly introduced organic ligand molecules are equivalent to increasing a number of the organic ligands on the surfaces of the QDs, thereby enhancing the colloidal stability and the dissolution dispersion of the QDs in a solvent, especially in an ink solvent system.

After a conventional QD preparation reaction finished, there are a large amount of dangling bonds exist on the surfaces of the QD, some of the dangling bonds are linked to a plurality of organic molecules added during the reaction (such as organic amine, organic carboxylic acid, organic phosphine, mercaptan, and more), while other of the dangling bonds are exposed to an external environment and easily reacts with the external environment. Also, the exposed dangling bonds may form a defect state and a defect energy level in a band gap, which is also an important reason causing the non-radiative transition loss. Therefore, an effective ligand exchange reaction is required to increase a number of the ligands on the surfaces of the QDs, and enhance a binding degree of the QDs to the surface ligands, so as to eliminate as much as possible the dangling bonds exposed on the surfaces of the QDs. By adding the ion-containing organic ligand precursors reacted in advance into an existing QD material, and by making an effective ligand exchange on the surfaces of the QDs through the ion-containing organic ligand precursors, the embodiments thereby achieve as much as possible the purpose of eliminating the exposed dangling bonds on the surfaces of the QDs.

Specifically, a preparation method for the QD provided in some embodiments includes a plurality of following steps:

providing a QD solution;

providing an ion-containing organic ligand precursor;

mixing the ion-containing organic ligand precursor and the QD solution, to make a ligand exchanging, before centrifuging and obtaining the QDs having the ligand exchanged.

The preparation method for the QD provided in some embodiments, by adding the ion-containing organic ligand precursors reacted in advance into an existing QD solution, and by making an effective ligand exchange on the surfaces of the QDs through the ion-containing organic ligand precursors, on one hand, achieves as much as possible the purpose of eliminating the exposed dangling bonds on the surfaces of the QDs, on other hand, since the ion combined with the exposed dangling bond has already connected itself to an organic ligand molecule, thus no new exposed dangling bonds will be introduced at a same time of the binding, thus it is able to effectively suppressing a defect state and a defect level, reduce a non-radiative transition loss, thereby improve a luminous efficiency of the QDs. Also, a newly introduced organic ligand molecule is equivalent to adding a number of the organic ligand on the surfaces of the QDs, therefore, it is possible to enhance a colloidal stability and a dissolution dispersibility of the QDs in the solvent, especially in an ink solvent system.

A method of exchanging the ligands, wherein the QD solution may be an untreated QD solution obtained after finishing another preparation process; may also be a solution system formed by re-dispersing a QD material obtained from another preparation process into an organic solvent, the organic solvent includes, but not limited to, chloroform, toluene, chlorobenzene, n-hexane, n-octane, decahydronaphthalene, tridecane, TOP, TBP, ODE, OA, ODA, TOA, OAm, and more, or a mixed solvent containing two or more of the organic solvents described above. A selection and a structure of the specific QDs are described in details above, and no more detailed description herein.

In a specific embodiment, the ion-containing organic ligand precursor is at least one cation-containing organic ligand precursor. A selection of the specific cations is described in details above, and no more detailed description herein.

An action mechanism of adopting the cation-containing organic ligand precursor to make a ligand exchange is: when the cation-containing organic ligand precursor is mixing and reacting with an existing QD solution system, the cations will combine with the exposed dangling bonds existing on the surfaces of the QDs, while an organic ligand molecule having combined with the cation will also combine to the surfaces of the QDs at a same time, thus a ligand exchange is achieved.

In a specific embodiment, the ion-containing organic ligand precursor is at least one anion-containing organic ligand precursor. A selection of the specific anions is described in details above, and no more detailed description herein.

An action mechanism of adopting the anion-containing organic ligand precursor to make a ligand exchange is: when the anion-containing organic ligand precursor is mixing and reacting with an existing QD solution system, the anions will combine with the exposed dangling bonds existing on the surfaces of the QDs, while an organic ligand molecule having combined with the anion will also combine to the surfaces of the QDs at a same time, thus a ligand exchange is achieved.

In a specific embodiment, the cation-containing organic ligand precursor or the anion-containing organic ligand precursor may be obtained through a following method: mixing the cation-containing precursor or the anion-containing precursor with the organic ligand, and reacting for a certain time under a certain temperature, a cation-containing organic ligand precursor or an anion-containing organic ligand precursor will be prepared. A detailed selection of the organic ligand, and a plurality of preparation process parameters have been described in details above, thus no more descriptions herein.

The method of exchanging the ligands, the ligand exchange is made according to a mass ratio of (0.01~100):1 when mixing the ion-containing organic ligand precursor (for example: the cation-containing organic ligand precursor or the anion-containing organic ligand precursor) and the QD, a preferred ratio range is (0.05-10):1. A reaction temperature of the ligand exchange is 10-400° C., a preferred range of the temperature is the room temperature of 25° C. to 380° C.; a time is 5 minutes to 10 hours, a preferred range of the time is 5 minutes to 60 minutes; an atmosphere of the ligand exchange is one of an inert atmosphere, an air atmosphere, a vacuum (with a pressure <100 Pa), a preferred atmosphere is an inert atmosphere, such nitrogen or argon.

By adding the cation-containing organic ligand precursors, or the anion-containing organic ligand precursors reacted in advance into an existing QD material, and by making an effective ligand exchange on the surfaces of the QDs through the cation-containing organic ligand precursors or the anion-containing organic ligand precursors, some embodiments achieve as much as possible the purpose of eliminating the exposed dangling bonds on the surfaces of the QDs. Eliminating the exposed dangling bonds on the surfaces of the QDs, it is possible to improve the luminous efficiency of the QDs themselves, additionally, introducing more organic ligands and combing more closely on the surfaces of the QDs, it is possible to enhance effectively a colloidal stability and a dissolution dispersibility of the QDs in the solvent.

Compared to a conventional method, an advantage of the preparation method above of the QDs is: making a ligand exchange after mixing the ion-containing organic ligand precursor and the QD, that is, introducing the organic ligand molecule is actually achieved by combining the ions and the dangling bonds; thus, on one hand, an extremely strict and fine reaction condition control of the organic ligand molecule reacting and combining directly with the QD material may be avoided, and on other hand, a problem that the organic ligand molecules are selective when combining to a plurality of surface atoms of the QDs is solved. At a same time, the method of exchanging ligands described above may effectively reduce a number of the dangling bonds existing on the surfaces of the QDs on one hand, and on other hand, since the ions combining with the exposed dangling bonds themselves have already connected to the organic ligand molecules (since they are added to the system in a form of the cation-containing or the anion-containing organic ligand precursor), thus no new exposed dangling bonds will be introduced at a same time of the combination, thus it is able to effectively suppressing a defect state and a defect level, reducing a non-radiative transition loss, thereby improving a luminous efficiency of the QDs. Also, the newly introduced organic ligand molecules are equivalent to increasing a number of the organic ligands on the surfaces of the QDs, thereby enhancing the colloidal stability and the dissolution dispersion of the QDs in a solvent, especially in an ink solvent system.

A step of the method is independent to a preparation process of the QD material itself, that is, it does not affect the preparation process of the QD material, and does not affect a core-shell structure and a component composition of the QD material itself; while the method owns a generality, and is able to be applied to various QD material systems before achieving a beneficial effect.

A QD, wherein the QD comprises a QD core and an ion-containing organic ligand, and an exposed dangling bond on the surface of the QD core is combined with anion in the ion-containing organic ligand.

Wherein the QD comprises a QD core and a cation-containing organic ligand, the exposed dangling bonds on the surfaces of the QD core combine with the cations in the cation-containing organic ligand.

Wherein the QD comprises a QD core and an anion-containing organic ligand, the exposed dangling bonds on the surfaces of the QD core combine with the anions in the anion-containing organic ligand.

An application of the QD, wherein the QD is applied to preparing a functional layer material for a plurality of semiconductor devices. The semiconductor devices comprise any one of an electroluminescent device, a photoluminescence device, a lighting device, a solar cell, a display device, a photodetector, a bioprobe, and a nonlinear optical device.

The QD provided by some embodiments achieves a more efficient QD material luminous efficiency, and satisfies more the comprehensive performance requirement of a semiconductor device and a corresponding display technology to the QD material, and is an ideal QD illumination material suitable for the semiconductor devices and the display technology.

Taking a display of an electroluminescent as an example, a QLED (QD Light Emitting Diodes) device, comprises a pair of electrodes, a holes injection layer, a holes transport layer, a QD light-emitting layer, an electrons transport layer, wherein the QD light-emitting layer comprises the QDs disclosed in some embodiments.

A QD electroluminescent device is capable of achieving an excellent device performance, such as: 1) a high luminance, 2) a low driving voltage, 3) a high device efficiency and more. The QLED device includes a top emission upright type QLED device and a top emission inverse type QLED device.

In a specific embodiment, the top emission upright type QLED device comprises in a sequence a substrate, a bottom electrode, a holes injection layer, a holes transport layer, a QD light-emitting layer, an electrons transport layer, and a top electrode, wherein the bottom electrode is an anode and the top electrode is a cathode.

In a specific embodiment, the top emission inverse type QLED device comprises in a sequence a substrate, a bottom electrode, an electrons transport layer, a QD light-emitting layer, a holes transport layer, a holes injection layer, and a top electrode, wherein the bottom electrode is a cathode and the top electrode is an anode.

Some embodiments further provide a preparation method for the QLED device, the preparation method is different according to a QLED device having a different structure, details are described below:

A preparation step of the top emission upright type QLED device is:

1). Preparing a bottom reflective electrode (ie, a bottom electrode) on a substrate, which may be, but not limited to, a glass or a PET substrate; the reflective electrode may be, but not limited to, an Al or an Ag electrode, the reflective electrode is an anode; a preferred thickness of the reflective electrode is from 30 to 800 nanometers.

2). Preparing a hole injecting layer and a holes transport layer sequentially on the bottom reflective electrode; a material of the hole injecting layer may be, but not limited to, PEDOT:PSS, $MoO_3$, $VO_2$ or $WO_3$. A material of the holes transport layer may be, but not limited to, an organic transport material such as poly-TPD, TFB, PVK, CBP and more, or an inorganic transport material such as NiO or $MoO_3$ etc. Both the holes injection layer and the holes transport layer may be prepared by a solution method including printing or spraying, or a vacuum method including vacuum evaporation or sputtering. The holes injection layer and the holes transport layer preferably have a thickness of 10 to 150 nm.

3). Preparing a QD light-emitting layer on the holes transport layer, and a material of the QD light-emitting layer is the QD described in some embodiments. A material of the QD light-emitting layer may be prepared by a solution method including printing and spraying. A preferred thickness of the QD luminescent layer is from 10 to 100 nanometers.

4). Preparing an electrons transport layer sequentially on the QD light-emitting layer, a material of the electrons transport layer may be, but not limited to, a plurality of inorganic materials including ZnO, $Cs_2CO_3$, $TiO_2$, $WO_3$, $SnO_2$, AlZnO, ZnSnO, InSnO, and at least one of organic materials such as $Alq_3$, TPBI (1,3,5-tris(N-phenylbenzimidazol-2-yl) benzene) or TAZ (3-(4-biphenyl)-4-phenyl-5-tert-butylphenyl-1,2,4-triazole). The electrons transport layer may be prepared by a solution method including printing or spraying, or a vacuum method including vacuum evaporation or sputtering. The electrons transport layer preferably has a thickness of 10 to 150 nm.

5). Preparing a top electrode on the electrons transport layer, and forming the QLED device. The top electrode may be, but not limited to, an ITO or a thin layer metal electrode, the top electrode is a cathode. A preferred thickness of the thin layer metal electrode is 5-50 nm; a preferred thickness of the ITO electrode is 20-300 nm.

A preparation step of the top emission upright type QLED device is:

1). Preparing a bottom reflective electrode (ie, a bottom electrode) on a substrate, which may be, but not limited to, a glass or a PET substrate; the bottom reflective electrode may be, but not limited to, an Al or an Ag electrode, the bottom electrode is a cathode; a preferred thickness of the bottom reflective electrode is from 30 to 800 nanometers.

2). Preparing an electrons transport layer on the substrate, a material of the electrons transport layer may be, but not limited to, ZnO, $Cs_2CO_3$, $TiO_2$, $WO_3$, $SnO_2$, AlZnO, ZnSnO, InSnO, and at least one of organic materials such as $Alq_3$, TPBI (1,3,5-tris(N-phenylbenzimidazol-2-yl)benzene) or TAZ(3-(4-biphenyl)-4-phenyl-5-tert-butylphenyl-1,2,4-triazole). The electrons transport layer may be prepared by a solution method including printing or spraying, or a vacuum method including vacuum evaporation or sputtering. The electrons transport layer preferably has a thickness of 10 to 150 nm.

3). Preparing a QD light-emitting layer on the electrons transport layer, and a material of the QD light-emitting layer is the QD described in the embodiments. A material of the QD light-emitting layer may be prepared by a solution method including printing and spraying. A preferred thickness of the QD luminescent layer is from 10 to 100 nanometers.

4). Preparing a hole injecting layer and a holes transport layer sequentially on the QD light-emitting layer. A material of the hole injecting layer may be, but not limited to, PEDOT:PSS, $MoO_x$, $VO_2$ or $WO_3$. A material of the holes transport layer may be, but not limited to, an organic transport material such as poly-TPD, TFB, PVK, NBP and more, or an inorganic transport material such as NiO or more. Both the holes injection layer and the holes transport layer may be prepared by a solution method including printing or spraying, or a vacuum method including vacuum evaporation or sputtering. The holes injection layer and the holes transport layer preferably have a thickness of 10 to 150 nm.

5) Preparing a top electrode on the electrons transport layer, and forming the QLED device. The top electrode may be, but not limited to, an ITO or a thin layer metal electrode, the top electrode is an anode. A preferred thickness of the thin layer metal electrode is 5-50 nm; a preferred thickness of the ITO electrode is 20-300 nm.

A QD ink disclosed in the embodiments, comprises the QDs described in the embodiments.

The QD ink, wherein, counting in a mass percentage, comprising:

the QD: 0.01-40.0%; the solvent: 60.0-99.99%, the solvent comprises at least one of the organic solvents.

Preferably, the solvent disclosed in some embodiments comprises 1-3 kinds of organic solvent. The organic solvent includes, but not limited to: an alkane, an aromatic organic solvent, an alcohol organic solvent and more. For example, the solvent in some embodiments of the present invention may be one solvent of a decalin, may be two solvents of the dodecane and 2-methylcyclohexanol, or may be three solvents of o-dichlorobenzene, phenylcyclohexane and 2-methyl cyclohexanol.

Preferably, a mass percentage of the QDs in the QD ink is 0.5-10%.

A boiling point range of the QD ink disclosed in some embodiments of the present invention is 50-300° C., preferably, the boiling point range of the QD ink is 100-250° C.

At a room temperature (25° C.), a viscosity range of the QD ink in some embodiments of the present invention is 0.5-40 cPs, and preferably, the viscosity range of the QD ink is 2.0-20 cPs.

At a room temperature (25° C.), a surface tension range of the QD ink in some embodiments of the present invention is 20-50 mN/m, and preferably, the surface tension range of the QD ink is 25-35 mN/m.

By adopting a system of the QD ink described above, some embodiments can realize a good film forming performance and a machinability property of the QD ink, especially a printability.

A plurality of examples are listed below for a detailed description to the embodiments.

Example 1

The preparation method of the QD in the present embodiment, comprising:

(1) preparing an InP/ZnS QD solution (with a volume of 20 ml, wherein a mass of the QD is about 200 mg);

(2) preparing a zinc oleate as a Zn cation ligand precursor, the zinc oleate as the cation ligand precursor in the present example is prepared by a following method: mixing 1 mmol of zinc acetate and 2.5 mmol of oleic acid and heating under an inert atmosphere to 170° C. and reacting for 30 minutes, before obtaining the zinc oleate in the present embodiment;

(3) under an inert atmosphere at 280° C., adding 2 mmol zinc oleate into an InP/ZnS QD solution, and keeping the temperature at 280° C. for 30 minutes for a reaction;

(4) carrying out a centrifugation after cooling to the room temperature: transferring a reaction mixture to a centrifuge tube, adding 30 ml of acetone, and centrifuging a system of a mixture solution at 8000 rpm for 5 minutes in a high-speed centrifuge; before discarding a liquid phase; re-dispersing a solid phase remained with an n-hexane, before using a same method and centrifuging once again, and discarding the liquid phase to obtain a purified high-efficiency QD with surfaces modified by the zinc oleate.

Example 2

The preparation method of the QD in the present embodiment, comprising:

(1) preparing a CdZnSe QD solution (with a volume of 25 ml, wherein a mass of the QD is about 150 mg);

(2) preparing an S-TOP as a S-anion ligand precursor, the S-TOP as the anion ligand precursor in the present example is prepared by a following method: mixing 1.5 mmol of S and 2 ml of TOP, and heating under an air atmosphere to 140° C. and reacting for 30 minutes, before obtaining the S-TOP in the present embodiment;

(3) under an inert atmosphere at 300° C., adding 1.5 mmol S-TOP into a CdZnSe QD solution, and keeping the temperature at 300° C. for 15 minutes for a reaction;

(4) carrying out a centrifugation after cooling to the room temperature: transferring a reaction mixture to a centrifuge tube, adding 30 ml of acetone, and centrifuging a system of a mixture solution at 8000 rpm for 3 minutes in a high-speed centrifuge; before discarding a liquid phase; re-dispersing a solid phase remained with n-hexane, before using a same method and centrifuging once again, and discarding the liquid phase to obtain a purified high-efficiency QD with surfaces modified by the S-TOP.

Example 3

The preparation method of the QD in the present embodiment, comprising:

(1) preparing an InP QD solution (with a volume of 5 ml, wherein a mass of the QD is about 20 mg);

(2) preparing a zinc oleamine as a Zn cation ligand precursor, the zinc oleate as the cation ligand precursor in the present example is prepared by a following method: mixing 1 mmol of zinc acetate and 1 ml oleylamine and heating under an inert atmosphere to 120° C. and reacting for 30 minutes, before obtaining the zinc oleamine in the present embodiment;

(3) under an air atmosphere at 80° C., adding 1.5 mmol zinc oleamine into a CdZnSe QD solution, and keeping the temperature at 80° C. for 60 minutes for a reaction;

(4) carrying out a centrifugation after cooling to the room temperature: transferring a reaction mixture to a centrifuge tube, adding 30 ml of acetone, and centrifuging a system of a mixture solution at 8000 rpm for 5 minutes in a high-speed centrifuge, before discarding a liquid phase; re-dispersing a solid phase remained with an n-hexane, before using a same method and centrifuging once again, and discarding the liquid phase to obtain a purified high-efficiency QD with surfaces modified by the zinc oleamine.

Example 4

Figure 1:
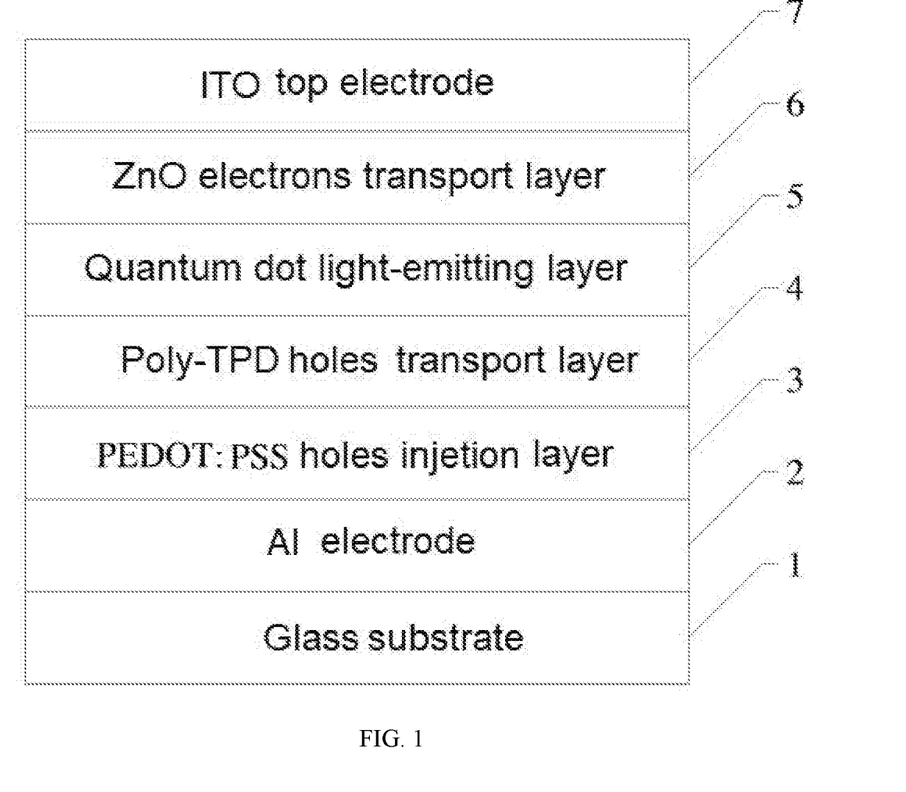
FIG. 1 illustrates a schematic diagram of a QD light-emitting diode disclosed in the example 4 of the present invention.

A QD light-emitting diode in the embodiments, shown as FIG. 1, comprising in a sequence from bottom up: a glass substrate 1, an Al electrode 2, a PEDOT:PSS holes injection layer 3, a poly-TPD holes transport layer 4, a QD light-emitting layer 5, a ZnO electrons transport layer 6 and an ITO top electrode 7.

A step of preparing the QD light emitting diode of the present example is as follows:

Preparing a 100 nm Al electrode by a vacuum evaporation on a glass substrate, then preparing a 30 nm PEDOT:PSS holes injection layer and a 30 nm poly-TPD holes transport layer in a sequence, and preparing a layer of the QD luminescent layer prepared by the QDs described in the embodiments 1-3 in the present disclosure on the poly-TPD holes transport layer, with a thickness of 20 nm, followed by preparing a 40 nm ZnO electrons transport layer on the QD light-emitting layer, and finally, preparing a 120 nm ITO by a sputtering method as a top electrode.

Example 5

Figure 2:
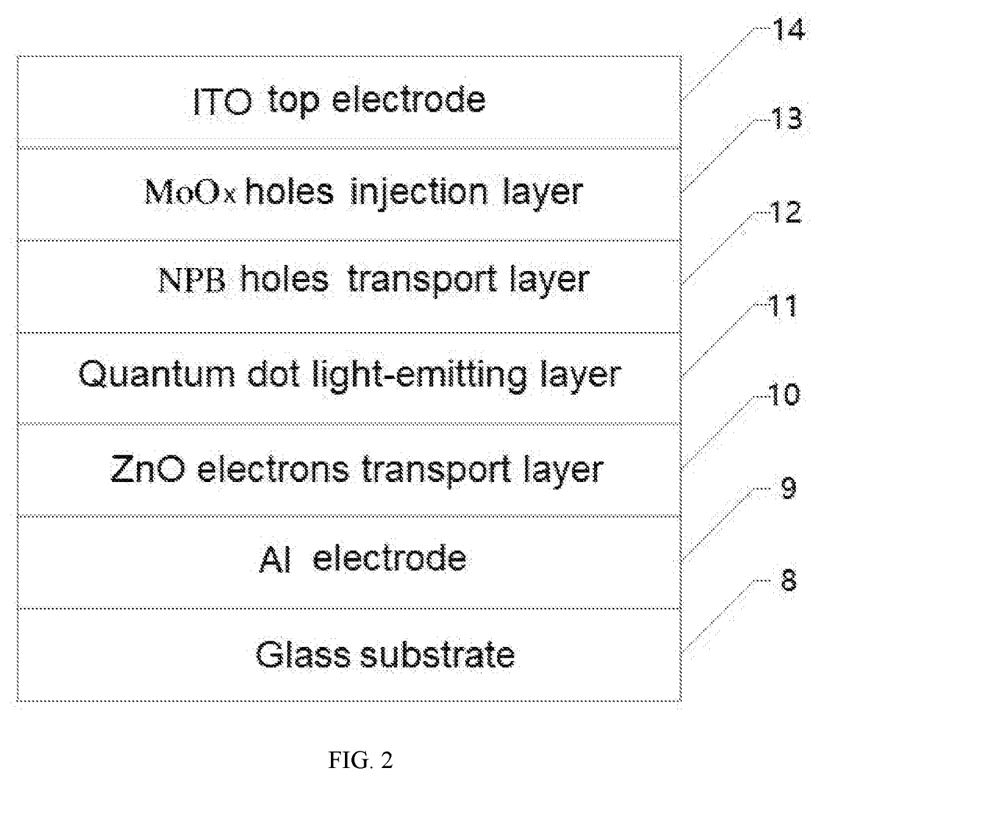
FIG. 2 illustrates a schematic diagram of a QD light-emitting diode disclosed in the example 5 of the present invention.

A QD light-emitting diode in the embodiments, shown as FIG. 2, comprising in a sequence from bottom up: a glass substrate 8, an Al electrode 9, a ZnO electrons transport layer 10, a QD light-emitting layer 11, a NPB holes transport layer 12, an MoOx holes injection layer 13 and an ITO top electrode 14.

A step of preparing the QD light emitting diode of the present example is as follows:

Preparing a 100 nm Al electrode by a vacuum evaporation on a glass substrate, then preparing a 40 nm electrons transport layer and a 20 nm QD luminescent layer in a sequence, before preparing a layer of a 30 nm NPB holes transport layer, a layer of a 5 nm $MoO_x$ holes injection layer by a method of the vacuum evaporation, and finally, preparing a 120 nm ITO by a sputtering method as a top electrode. The material of the QDs in the QD light emitting layer is the QD light emitting layers obtained by the QD preparation in the examples 1-3.

Example 6

A method of exchanging the QD ligands, comprising:

(1) providing a CdSe/ZnS QD solution (with a volume of 25 ml, wherein a mass of the QDs is about 600 mg);

(2) providing a zinc oleate with a cation ligand precursor having a C1-L1 structure (C1=Zn, L1=OA), the zinc oleate with the cation ligand precursor in the present example is prepared by a following method: mixing 1 mmol of zinc acetate and 2.5 mmol of oleic acid, and heating to 170° C. for 30 minutes under an inert atmosphere, before obtaining a zinc oleate of the present example;

(3) under an inert atmosphere at 300° C., adding the zinc oleate into a CdSe/ZnS QD solution, keeping the temperature at 300° C. and making the ligand exchange for 60 minutes;

(4) carrying out a centrifugation after cooling to the room temperature: transferring a mixture solution after the ligands exchanged to a centrifuge tube, adding 30 ml of acetone, and centrifuging a system of the mixture solution at 8000 rpm for 5 minutes in a high-speed centrifuge, before discarding a liquid phase; re-dispersing a solid phase remained with an n-hexane, before using a same method and centrifuging once again, and discarding the liquid phase to obtain a purified high-efficiency QD sample.

Example 7

A method of exchanging the QD ligands, comprising:

(1) providing a CdZnSe QD solution (with a volume of 25 ml, wherein a mass of the QDs is about 150 mg);

(2) providing S-TOP with an anion ligand precursor having a C1-L1 structure (C1=S, L1=TOP), the S-TOP with the anion ligand precursor in the present example is prepared by a following method: mixing 1.5 mmol of S and 2 ml of TOP, and heating to 140° C. for 30 minutes under an air atmosphere, before obtaining the S-TOP of the present embodiment;

(3) under an inert atmosphere at 280° C., adding the S-TOP into a CdZnSe QD solution, keeping the temperature at 280° C. and making the ligand exchange for 15 minutes;

(4) carrying out a centrifugation after cooling to the room temperature: transferring a mixture solution after the ligands exchanged to a centrifuge tube, adding 30 ml of acetone, and centrifuging a system of the mixture solution at 8000 rpm for 3 minutes in a high-speed centrifuge, before discarding a liquid phase; re-dispersing a solid phase remained with an n-hexane, before using a same method and centrifuging once again, and discarding the liquid phase to obtain a purified high-efficiency QD sample.

Example 8

A method of exchanging the QD ligands, comprising:

(1) providing a InP/ZnS QD solution (with a volume of 5 ml, wherein a mass of the QDs is about 100 mg);

(2) providing a zinc oleamine with a cation ligand precursor having a C1-L1 structure (C1=Zn, L1=OAm), the zinc oleamine with the cation ligand precursor in the present example is prepared by a following method: mixing 1 mmol of zinc acetate and 1 ml of oleylamine, and heating to 120° C. for 30 minutes under an inert atmosphere, before obtaining a zinc oleamine of the present example;

(3) under an inert atmosphere at 120° C., adding the zinc oleamine into an InP/ZnS QD solution, keeping the temperature at 120° C. and making the ligand exchange for 5 minutes;

(4) carrying out a centrifugation after cooling to the room temperature: transferring a mixture solution after the ligands exchanged to a centrifuge tube, adding 30 ml of acetone, and centrifuging a system of the mixture solution at 8000 rpm for 3 minutes in a high-speed centrifuge, before discarding a liquid phase; re-dispersing a solid phase remained with an n-hexane, before using a same method and centrifuging once again, and discarding the liquid phase to obtain a purified high-efficiency QD sample.

Example 9

A QD ink, comprising any one or several high efficient QDs as described in the examples 6-8 in the embodiments, and the solvent is decalin. The QD ink in the embodiments is prepared by a following method: adding 100 mg of the QD (with a surface ligand of OA(oleic acid)) into 10 mL of decalin, stirring a mixture for 30 minutes, before obtaining the QD ink.

Example 10

A QD ink, comprising any one or several high efficient QDs as described in the examples 6-8 in the embodiments, and the solvent is a mixture solvent composed by two solvents of a dodecane and a 2-methylcyclohexanol, wherein a volume ratio between the dodecane and the 2-methylcyclohexanol is 1:1. The QD ink in the embodiments is prepared by a following method: adding 100 mg of the QD (with a surface ligand of octylmercaptan) into a mixture solvent of 2.5 mL of dodecane and 2.5 mL 2-methylcyclohexanol, stirring a mixture for 30 minutes, before obtaining the QD ink.

Example 11

A QD ink, comprising any one or several high efficient QDs as described in the examples 6-8 in the embodiments, and the solvent is a mixture solvent composed by three solvents of an o-dichlorobenzene, a phenylcyclohexane and a 2-methylcyclohexanola, wherein a volume ratio of the o-dichlorobenzene, the phenylcyclohexane and the 2-methylcyclohexanola is 1:4:5. The QD ink in the embodiments is prepared by a following method: adding 100 mg of the QD (with a surface ligand of TOP) into a mixture solvent of 0.3 mL of o-dichlorobenzene, 1.2 mL of phenylcyclohexane and 1.5 mL of 2-methylcyclohexanola, stirring a mixture for 30 minutes, before obtaining the QD ink.

All above, the present disclosure provides a QD and a preparation method thereof. Through adding the ion-containing organic ligand precursor to the QD solution, and making a reaction between the ion-containing organic ligand precursor and the QD, the present disclosure achieves a purpose of eliminating the exposed dangling bonds on the surfaces of the QD as possible. The present disclosure achieves an efficient surface ligand exchange through exchanging the surface ligands by the ion-containing organic ligand precursor based on an existing QD material (for example, the cation-containing or the anion-containing organic ligand precursor), and eliminates effectively the exposed dangling bonds on the surfaces of the QDs. Reducing the exposed dangling bonds on the surfaces of the QDs as described in the present disclosure, may improve a self-luminous property of the QD material, making it more suitable for an application in a display, an illumination, a biomarker, and more. At a same time, the method in the present disclosure is independent to the preparation process of the QD material itself, and will not affect the preparation process of the QD material, or affect the core-shell structure and the component composition of the QD material. In addition, the method disclosed in the present disclosure has a universality, which is not only being able to be applied to various QD material systems, but being able to be applied to various surface ligand molecule. At a same time, the highly efficient QD material obtained is able to satisfy more the comprehensive performance requirement of a semiconductor device and a corresponding display technology to the QD material, and is an ideal QD illumination material suitable for the semiconductor devices and the display technology. Based on the invention, it is possible to introduce various types of surface ligand molecules, and according to a principle of "like dissolves like", a suitable surface ligand molecule can be selected according to a kind of the solvent in the QD solution or the QD ink, and a ligand exchange can be carried out according to the method described above, so as to achieve a preparation of various types of the QD solutions and the QD inks.

It should be understood that the application of the present disclosure is not limited to the above examples and can be improved or transformed by those skilled in the art based on the above description. All these improvements and transformations should fall within the protection scope of the appended claims of the present disclosure.

What is claimed is:

1. A preparation method of a quantum dot (QD), comprising:
   preparing a QD solution;
   mixing an ionic precursor and an organic ligand for a reaction in which ions in the ionic precursor are combined with the organic ligand, to prepare an ion-containing organic ligand precursor, wherein the organic ligand in the ion-containing organic ligand precursor is at least one of an organic phosphine, an organic amine, and an alkyl mercaptan;
   obtaining the ion-containing organic ligand precursor from the reaction;
   adding the ion-containing organic ligand precursor into the QD solution, and making a surface-modification to the QDs using the ligand precursor, before obtaining the QDs having the surfaces modified,
   wherein the ion-containing organic ligand precursor is at least one cation-containing organic ligand precursor, the cation in the cation-containing organic ligand precursor is at least a cation of a group IIB metal, a cation of a group IIIA element, a cation of a group IB meta or a rare-earth metal cation.

2. The preparation method of the QD according to claim 1, wherein the QDs in the QD solution are at least one QD in groups of II-VI, groups of III-V, and groups of IV-VI.

3. The preparation method of the QD according to claim 1, wherein a structure of the QDs in the QD solution is at least one of a homogenous multi-alloy component mononuclear structure, a multi-alloy component gradient mononuclear structure, a multi-alloy component discrete core-shell structure, a multi-alloy component gradient core-shell structure.

4. The preparation method of the QD according to claim 1, wherein the ionic precursor and the organic ligand are mixed at a molar ratio of an ionic element to the organic ligand of 1:0.1 to 1:10 for the reaction; a temperature of the reaction is 20-400° C. a time is 5 minutes to 10 hours, and an atmosphere of the reaction is one of an inert atmosphere, an air atmosphere, and a vacuum.

5. The preparation method of the QD according to claim 1, wherein the ion-containing organic ligand precursor and the QD are mixed at a mass ratio of (0.01-100):1 to make the surface-modification; a temperature of a reaction of the surface-modification is 10-400° C., a time is 5 minutes to 10 hours; and an atmosphere of the reaction of the surface-modification is one of an inert atmosphere, an air atmosphere, and a vacuum.

6. The preparation method of the QD according to claim 1, wherein an atmosphere of the reaction of mixing the ionic precursor and the organic ligand is one of an air atmosphere and a vacuum.

7. A preparation method of a QD, comprising:
   providing a QD solution;
   mixing an ionic precursor and an organic ligand for a reaction in which ions in the ionic precursor are combined with the organic ligand, to prepare an ion-containing organic ligand precursor, wherein the organic ligand in the ion-containing organic ligand precursor is at least one of an organic phosphine, an organic amine, and an alkyl mercaptan;
   obtaining the ion-containing organic ligand precursor prepared from the reaction;
   mixing the ion-containing organic ligand precursor and the QD solution to make a ligand exchanging, obtaining the ligand exchanged QDs,
   wherein the ion-containing organic ligand precursor is at least one cation-containing organic ligand precursor, the cation in the cation-containing organic ligand precursor is at least a cation of a group IIB metal, a cation of a group IIIA element, a cation of a group IB metal, or a rare-earth metal cation.

8. The preparation method of the QD according to claim 7, wherein the QDs in the QD solution are at least one QD in groups of groups of III-V, and groups of IV-VI.

9. The preparation method of the QD according to claim 7, wherein the ion-containing organic ligand precursor and the QD are mixed at a mass ratio of (0.01-100):1 to make the ligand exchanging; a reaction temperature of the ligand exchanging is 10-400° C., a time is 5 minutes to 10 hours; and an atmosphere of the ligand exchanging is one of an inert atmosphere, an air atmosphere, and a vacuum.

10. The preparation method of the QD according to claim 7, further comprising:
    carrying out a centrifugation after mixing the ion-containing organic ligand precursor and the QD solution, to obtain the ligand exchanged QDs.

11. A QD, wherein the QD comprises a QD core and an ion-containing organic ligand, and an exposed dangling bond on the surfaces of the QD core is combined with an ion in the ion-containing organic ligand,
    wherein the QD includes a ligand exchanged QD obtained from an ion-containing organic ligand precursor; and the ion-containing organic ligand precursor is at least one cation-containing organic ligand precursor, the cation in the cation-containing organic ligand precursor is at least a cation of a group IIB metal, a cation of a group IIIA element, a cation of a group IB metal, or a rare-earth metal cation,
    wherein the ion-containing organic ligand precursor is prepared by mixing an ionic precursor and the organic ligand for a reaction in which the ions in the ionic precursor are combined with the organic ligand, and the organic ligand in the ion-containing organic ligand precursor is at least one of an organic phosphine, an organic amine, and an alkyl mercaptan.

* * * * *